(12) United States Patent
Williams et al.

(10) Patent No.: US 6,292,535 B1
(45) Date of Patent: Sep. 18, 2001

(54) DIGITAL X-RAY IMAGING SYSTEM WITH AUTOMATIC DISPLAY IMAGE GREYSCALE ENHANCEMENT AND METHOD

(75) Inventors: Neil A. Williams, Los Gatos; Gerald A. May, Saratoga, both of CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/468,744

(22) Filed: Dec. 21, 1999

(51) Int. Cl.[7] .................................................. H05G 1/64
(52) U.S. Cl. ............................ 378/98.8; 382/254; 378/62
(58) Field of Search ............................... 378/62, 87, 98.7, 378/98.8; 382/168, 169, 254, 274

(56) References Cited

U.S. PATENT DOCUMENTS 6,108,453 * 8/2000 Acharya ................................ 382/254

* cited by examiner

Primary Examiner—Robert H. Kim
Assistant Examiner—Courtney Thomas
(74) Attorney, Agent, or Firm—Paul Hentzel (57) ABSTRACT

Digital X-ray imaging system 10 automatically provides an enhanced digital display image 10D from a digital camera image 10C showing internal structure 10S of interest within subject 11S. Calibrated radiation attenuators 10A placed near the subject appear in the camera image and in the display image. X-ray source 10X generates X-ray radiations which are attenuated within the calibrated attenuators to provide calibrated attenuations. The X-ray radiations are also differentially attenuated within the interior of the subject to reveal internal structure therein. Digital X-ray camera 11C detects the calibrated radiations to form the camera image of the calibrated greyscale levels. The camera also detects the differentially attenuated radiations to provide the camera image of internal structure of the subject. Each calibrated attenuator appears in the camera image as a collection of adjacent camera pixels exhibiting one of the plurality of calibrated greyscale levels within the camera greyscale. Retriever 12 retrieves the calibrated greyscale level from the digital camera image of each attenuator pixel collection. Greyscale coordinator 14 is responsive to the retrieved calibrated greyscale levels for determining mapping assignments defining the relationship between the camera greyscale and the display greyscale which provides the enhanced digital display image. Greyscale mapper 11M is responsive to the mapping assignments for mapping the camera greyscale levels of the camera pixels forming the camera image into display greyscale levels of display pixels forming the enhanced display image. Display monitor 11D is responsive to the enhanced display image for displaying a pixel image of the internal structure of interest within the subject.

32 Claims, 5 Drawing Sheets

DIGITAL X-RAY IMAGING SYSTEM WITH AUTOMATIC DISPLAY IMAGE GREYSCALE ENHANCEMENT AND METHOD

TECHNICAL FIELD

This invention relates to digital X-ray imaging, and more particularly to such imaging which provides an enhanced greyscale digital display image from a digital camera image.

BACKGROUND

Heretofore, radiologists manually adjusted the brightness and contrast of the display image to suit the radiologists visual preference, and to accommodate the nature of the internal structure being examined. Variation in X-ray intensity at the detector camera varied due to such factors as manufacturing tolerances, tube aging, detector position, and patient body type. This radiation variation caused shifts in the greyscale of the camera image. An increase in radiation promoted an over exposed light images, and a decrease in radiation promoted an under exposed dark image.

A calibrating wedge of known attenuation was imaged permitting the radiologist to manually calibrate the display image. The calibrating wedge had a thick high attenuation end simulating bone structure which attenuated radiation producing an under exposed light image. The calibrating wedge also had a thin low attenuation end simulating soft tissue which readily passed radiation producing an over exposed dark image. The radiologists used these light and dark images (and the greyscale tones therebetween) as a guide to adjusting the display image.

SUMMARY

It is therefore an object of this invention to provide a digital X-ray imaging system and method which automatically compensates for light and dark images to provide an enhanced digital display image formed by display greyscale from a digital camera image formed by camera greyscale.

It is another object of this invention to provide such a system and method which automatically selects a dynamic range from the camera image to conform to the display dynamic range available on the display monitor. The dynamic range of any particular camera image is usually much less than the full greyscale range of the camera. The camera has unused light greyscale levels above the opaqueness of interest, and unused dark greyscale levels below the transparency of interest. This underemployment of greyscale levels is not passed on the display image. Every greyscale level of the display image is employed as a greyscale level within the selected dynamic range. None of the display greyscale levels are wasted on these opaque and near opaque light tones, and on transparent and near transparent dark tones. All of the display image greyscale levels are in the range of the internal structure of interest.

It is a further object of this invention to provide such a system and method which automatically enhances the display image in response to the highest and lowest calibrated attenuator.

It is a further object of this invention to provide such a system and method which automatically enhances the display image in response to calibrated attenuators dedicated to various body types.

It is a further object of this invention to provide such a system and method which locates the collection of pixels forming each calibrated attenuator image within the digital camera image for identifying the particular calibrated greyscale level exhibited by that calibrated attenuator. The camera image address of each pixel collection is determined from the location, permitting the collection to be retrieved for analysis.

It is a further object of this invention to provide such a system and method which eliminates irregular boundary effects along the edge of the attenuator pixel collection. A peripheral region of suspect outer pixels is discarded leaving a main region of reliable inner pixels.

It is a further object of this invention to provide such a system and method which corrects camera greyscale distortion. A series of calibrated attenuator with known attenuations exhibits a corresponding series of greyscale levels. The greyscale intervals between the greyscale levels can be corrected to match the attenuation intervals between the calibrated attenuators.

Briefly, these and other objects of the present invention are accomplished by automatically enhancing a digital display image formed by display greyscale from a digital camera image formed by camera greyscale showing internal structure of interest within a subject. A plurality of calibrated attenuators are provided each having an attenuation which has been calibrated against a known reference attenuation. X-ray radiations are generated at least some of which are calibratedly attenuated within the interior of the calibrated attenuators, and other of which are differentially attenuated within the interior of the subject to reveal internal structure thereof. The plurality of calibrated attenuators and the subject are exposed to the generated X-ray radiations to effect the calibrated attenuated radiations within the calibrated attenuators, and to produce the differentially attenuated radiations within the subject. Detection of the calibrated attenuated radiations provides a plurality of calibrated greyscale levels. Detection of the differentially attenuated radiations provides the digital camera image of internal structure of the subject formed by pixels at greyscale levels within the camera greyscale. Each calibrated attenuator appears in the digital camera image as a collection of adjacent camera pixels exhibiting one of the plurality of calibrated greyscale levels within the camera greyscale. A calibrated greyscale level is retrieved from the digital camera image for each of the attenuator pixel collections. The greyscale is coordinated in response to the retrieved calibrated greyscale levels for determining mapping assignments defining the relationship between the camera greyscale and the display greyscale. The greyscale is mapped in response to the mapping assignments from the coordinator for mapping the camera greyscale levels of the camera pixels forming the digital camera image into display greyscale levels of display pixels forming the enhanced display image. The enhanced display image is displayed employing the display greyscale showing the internal structure of interest within the subject.

BRIEF DESCRIPTION OF THE DRAWINGS

Further objects and advantages of the present imaging system and method and the greyscale enhancement of the display image will become apparent from the following detailed description and drawings (not drawn to scale) in which.

The first digit of each reference numeral in the above figures indicates the figure in which an element or feature is most prominently shown. The second digit indicates related elements or features, and a final letter (when used) indicates a sub-portion of an element or feature.

REFERENCE NUMERALS IN DRAWINGS

The table below lists the reference numerals employed in the figures, and identifies the element designated by each numeral.

10 Digital X-ray Imaging System 10
   10A Calibrated Radiation Attenuators 10A
   10C Digital Camera Image 10C
   10D Digital Display Image 10D
   10M Bit Map 10M
   10S Internal Structure 10S
   10X X-ray Source 10X
   11C Digital X-ray Camera 11C
   11D Display Monitor 11D
   11M Greyscale Mapper 11M
   11S Subject 11S
12 Calibrated Greyscale Retriever 12
14 Greyscale Coordinator 14
32 Calibrated Greyscale Retriever 32
   32A Greyscale Averager 32A
   32L Collection Locator 32L
   32R Average Rounder 32R
34 Greyscale Coordinator 34
   34A Greyscale Assignor 34A
   34C Greyscale Interval Checker 34C
   34D Interval Corrector 34D
42 Calibrated Greyscale Retriever 42
   42A Greyscale Analyzer 42A
   42M Template Memory 42M
   42R Pattern Recognizer 42R
   42S Greyscale Sorter 42S
   42T Boundary Trimmer 42T
46 Pixel Collection 46
   46P Peripheral Pixel Region 46P
   46M Main Pixel Region 46M

Figure 1:
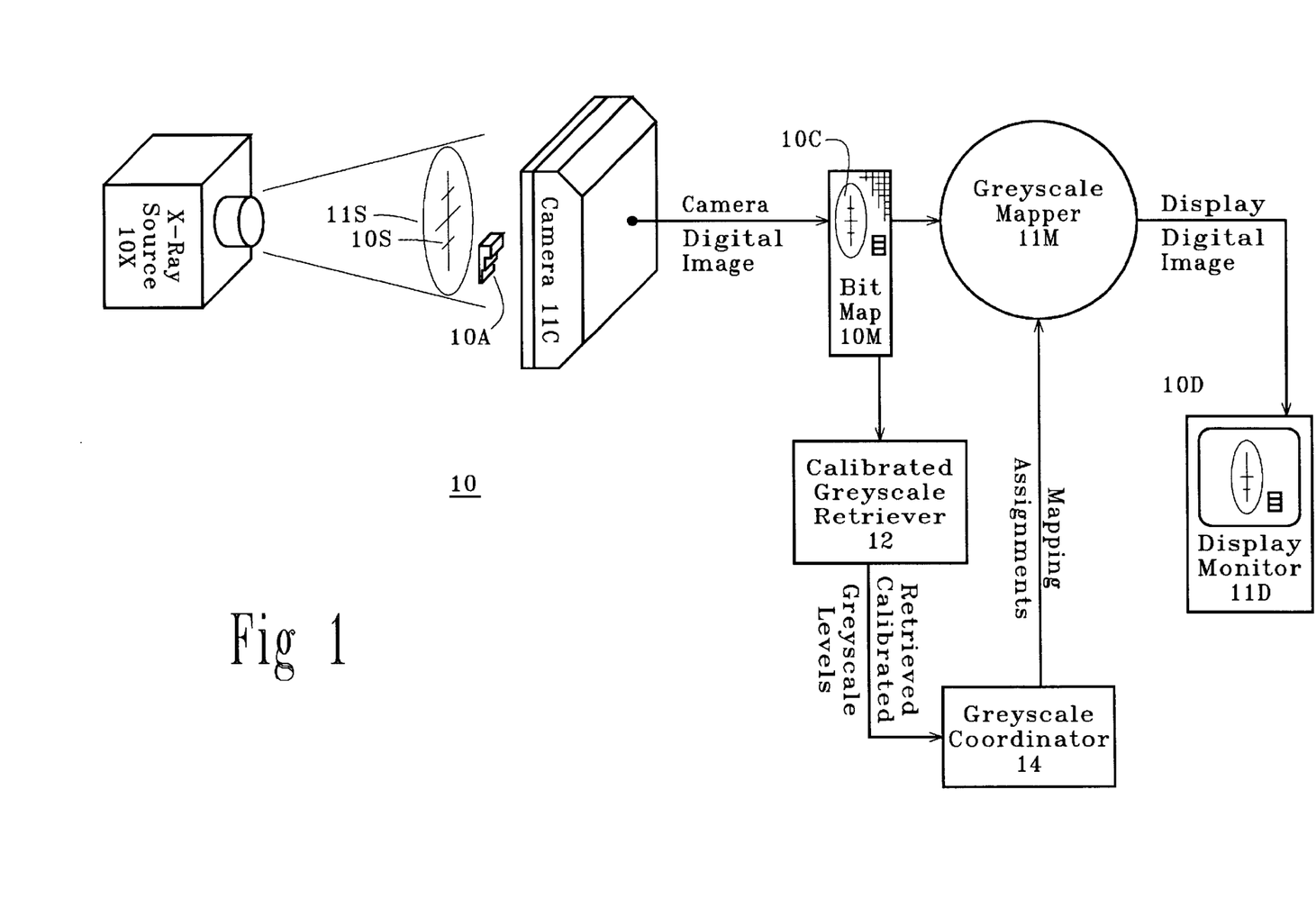
FIG. 1 is a block diagram of a digital X-ray imaging system 10 including stepped calibrated attenuators 10A, calibrated greyscale retriever 12, and greyscale coordinator 14.

GENERAL EMBODIMENT (FIG. 1)

Digital X-ray imaging system 10 automatically provides an enhanced digital display image 10D formed by display greyscale from a digital camera image 10C formed by camera greyscale in bit map 10M. The enhanced digital display image shows internal structure 10S of interest within subject 11S. The subject may be an entire patient (or package or suitcase), or an organ within a patient or simply a part of an organ. The internal structure of interest may be any part of the interior of the subject. A plurality of C calibrated radiation attenuators 10A placed near the subject appear in the camera image and in the display image. The calibrated attenuators may be formed by steps in a monolithic attenuator, or each attenuator may be a separate piece of attenuator material. Each of the calibrated attenuator steps has been previously calibrated against a known reference attenuation under reference radiations condition.

X-ray source 10X generates X-ray radiations which are attenuated within the calibrated attenuators to provide calibrated attenuations. The X-ray radiations are also differentially attenuated within the interior of the subject to reveal internal structure therein. Some of the attenuation may be due to direct absorption of the radiations within the mass of the attenuator or subject. Some of the attenuation may be due to merely scattering of the radiations, which prevents those radiations from contributing to the formation of the camera image.

Digital X-ray camera 11C detects the calibrated radiations to form the camera image of the plurality of calibrated greyscale levels. The camera also detects the differentially attenuated radiations to provide the camera image of internal structure of the subject. The camera image is formed by pixels at greyscale levels within the camera greyscale range (see FIG. 2). Each calibrated attenuator appears in the camera image as a collection of adjacent camera pixels exhibiting one of the plurality of calibrated greyscale levels within the camera greyscale. The greyscale level associated with each calibrated attenuator is an effect caused primarily by the mass of the attenuator. This greyscale level is not an attribute or property of the calibrated attenuator, but is merely exhibited by the calibrated attenuator under reference radiation conditions. Similarly, the internal structure of the subject also appears as pixels in the camera image exhibiting camera greyscale levels. The X-ray camera defines a field of view which includes the calibrated attenuators and the subject. The camera may be any suitable imaging mechanism for detecting and digitizing the attenuated radiations, such as a charge coupled device array or a thin film transistor array.

Retriever 12 retrieves the calibrated greyscale level from the digital camera image of each attenuator pixel collection. Greyscale coordinator 14 is responsive to the retrieved calibrated greyscale levels for determining mapping assignments defining the relationship between the camera greyscale and the display greyscale which provides the enhanced digital display image. Greyscale mapper 11M is responsive to the mapping assignments for mapping the camera greyscale levels of the camera pixels forming the camera image into display greyscale levels of display pixels forming the enhanced display image. A suitable pixel display device such as display monitor 11D is responsive to the enhanced display image for displaying a pixel image of internal structure of interest within the subject.

Figure 2:
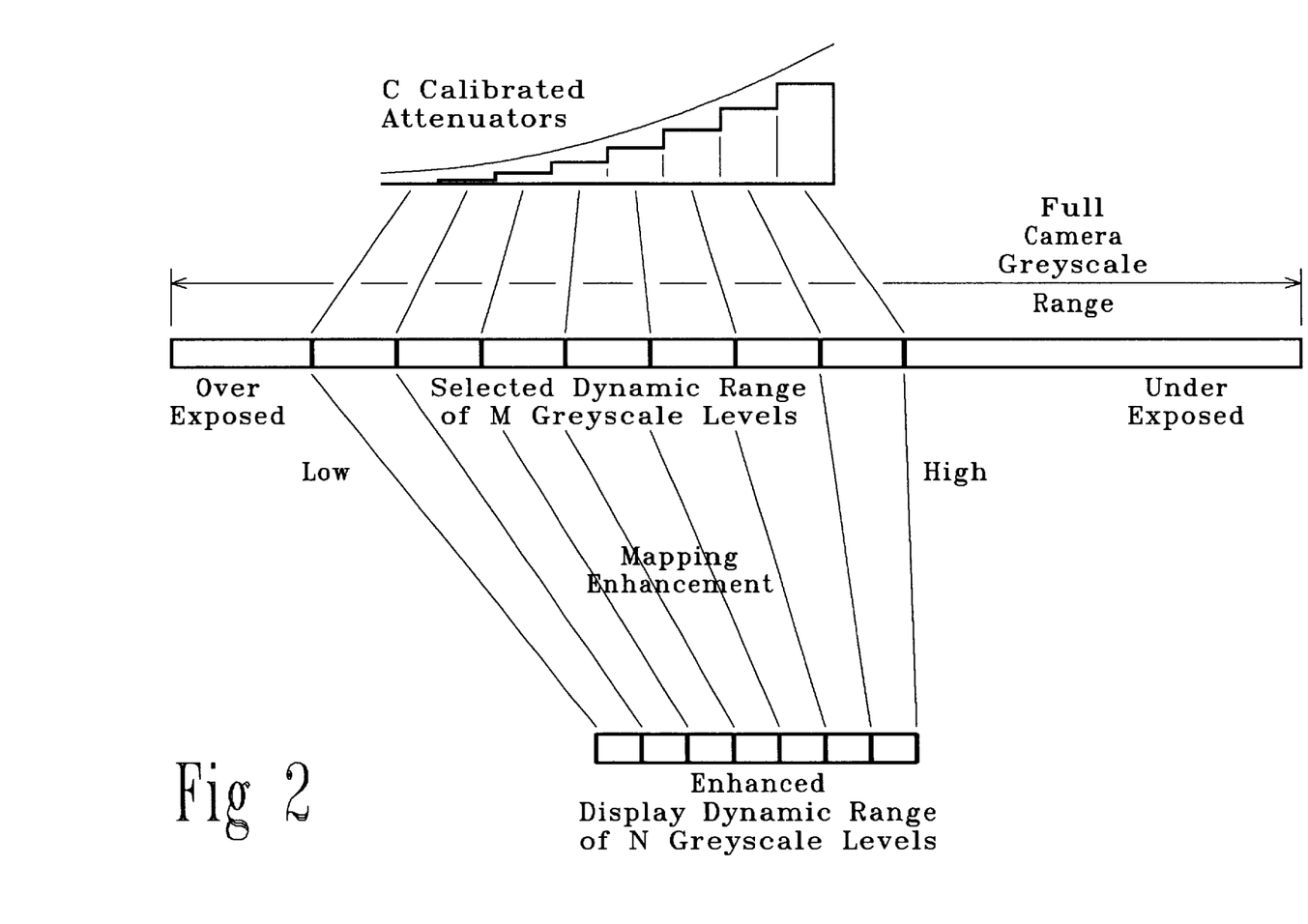
FIG. 2 is a greyscale dynamic range chart showing the dynamic range of the digital camera image selected from the full camera greyscale range, and the dynamic range of the digital display image.

The plurality of C calibrated attenuators includes a high attenuator with a high attenuation exhibiting a high calibrated greyscale level near the maximum opacity of internal structure of interest within the subject (see FIG. 2). Dense high mass foreign matter such as pennies has an opacity greater than this opacity of interest. The calibrated attenuators also includes a low attenuator with a low attenuation exhibiting a low calibrated greyscale level near the maximum transparency of internal structure of interest within the subject. Low mass matter such as air is more transparent than this transparency of interest. The camera greyscale levels exhibited by internal structure of interest extend from the high attenuation calibrated greyscale level to the low attenuation calibrated greyscale level defining a selected dynamic range of "M" camera greyscale levels which includes the C calibrated greyscale levels. The enhanced digital display image displayed on the pixel display monitor has a high enhanced greyscale level mapped from the high calibrated greyscale level, and a low enhanced greyscale level mapped from the low calibrated greyscale level. The enhanced greyscale levels of the display image extend from the high greyscale level to the low greyscale level defining a dynamic range of "N" display greyscale levels.

Calibrated Greyscale Levels

The calibration of the calibrated attenuators involves comparing the attenuated radiation from each attenuator with the attenuated radiation from a known reference material. Each type of calibrated attenuator such as adult front, adult side, child, frail elderly etc. has a separate attenuation scale and is calibrated independently. For example, two centimeters of normal adult bone material may be employed as the reference for calibrating the high attenuator for an adult front type calibrated attenuator. The high attenuator for a child type calibrated attenuator should be referenced against a much thinner reference. The low attenuator reference for the child calibrated attenuator is also less than the low attenuator reference for the adult. The attenuation range between these high and low references captures the structure of interest for the body type of each patient.

DYNAMIC RANGE CHART (FIG. 2)

The dynamic range chart of FIG. 2 shows the selected dynamic range of M greyscale levels for the digital camera image and the smaller dynamic range of N greyscale levels for the digital display image. The selected dynamic range extends only across the middle portion of the full camera greyscale range depending on the X-ray application. The display dynamic range preferably extends the full range of the display monitor. The full camera range might typically have 4,096 greyscale levels for example, which is much larger than the full display range which might typically be 256 or 512 greyscale levels. Generally, X-ray cameras have more detection intensity levels then can be readily discerned by the human eye.

The intensity of the radiations decrease exponentially with distance through the calibrated attenuators. Therefore, in order to have linearly spaced calibrated greyscale levels along the selected dynamic range (shown in FIG. 2), the thickness of the calibrated attenuators must increase exponentially (also shown in FIG. 2). The greyscale levels of intensity could include false colors assigned by the greyscale coordinator (pseudo color mapping) and generated by the monitor.

Figure 3:
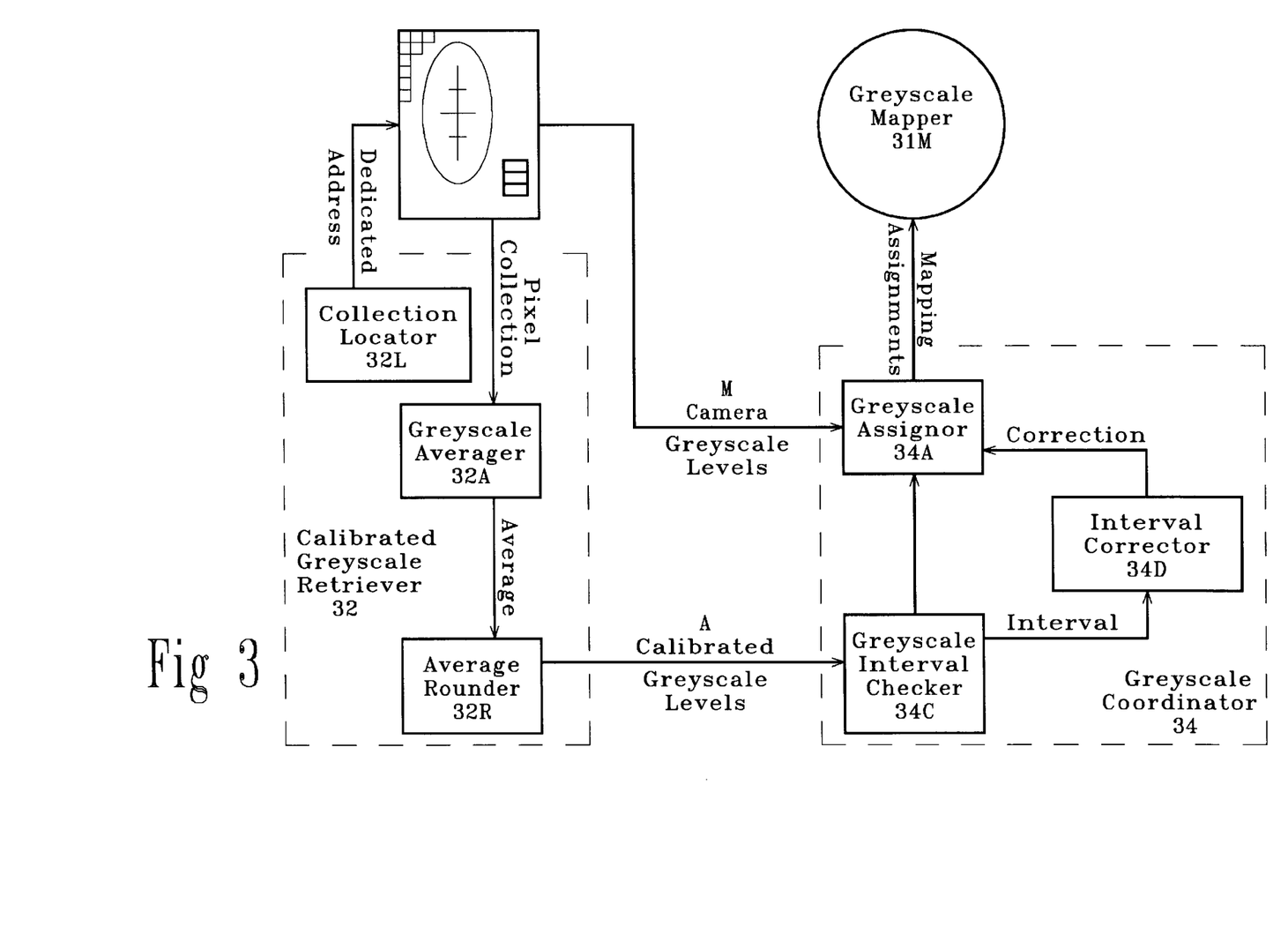
FIG. 3 is a block diagram of calibrated greyscale retriever 32 showing greyscale averaging of the pixels in the image of each calibrated attenuator, and greyscale coordinator 34 showing correction of camera greyscale distortion.

ATTENUATOR COLLECTION LOCATION (FIGS. 3 and 4)

The calibrated greyscale retriever provides the address of each attenuator pixel collection within the digital camera image corresponding to the position of each calibrated attenuator. The calibrated greyscale levels are retrieved the camera image at the determined addresses. In a fixed position embodiment shown in FIG. 3, the position of each calibrated attenuator is fixed relative to the camera causing each attenuator pixel collection to have a corresponding dedicated address within the camera image. Collection locator 32L merely provides the dedicated addresses from memory and the attenuator pixel collections are retrieved.

In a variable position embodiment shown in FIG. 4, the position of each calibrated attenuator may be variable relative to the camera causing each attenuator pixel collection to have a corresponding variable address within the camera image. The location of each attenuator pixel collection may be determined by pattern recognizer 42R in cooperation with templates in memory 42M. The template memory contains templates of predetermined pattern arrangements of the styles and types of each plurality of attenuators. That is, the calibrated attenuators forming each plurality are arranged in a predetermined configuration relative to one other. The embodiment of FIG. 4A shows a five attenuator configuration arranged in an easy to recognize cross pattern. Many other patterns may be employed with different numbers of calibrated attenuators. The pattern recognizer matches one of the templates and to shapes within the camera image, in order to recognize the predetermined pattern of the attenuator pixel collections. The pattern recognition may be size and orientation insensitive. The collection addresses are determined from the position of the recognized pixel collections within the camera image, and the attenuator pixel collections are retrieved.

AVERAGING EMBODIMENT (FIG. 3)

Greyscale averager 32A determines the average value of the greyscale levels within each attenuator pixel collection. Average rounder 32R reduces the average to an integer value indicating a single greyscale level. Under ideal conditions, all of the pixels within each collection would have the same greyscale level, and average-rounding would not be necessary. However, due to various non-ideal effects such as irregular boundaries, sensor interpolation, A/D truncation, and round-off,the pixel greyscale value may vary across a single collection. The median greyscale value of the pixels or other statistical valuation such as the prevailing value or most frequent value may be used instead of the average value.

GREYSCALE COMPRESSION (FIG. 3)

Greyscale assignor 34A within greyscale coordinator 34 assigns the M camera greyscale levels of the selected dynamic range among the N display greyscale levels of the display dynamic range, permitting the mapper to map the digital camera image into the enhanced digital display image. As shown in the in FIG. 2 embodiment, the selected dynamic range of M camera greyscale levels has more greyscale levels than the display dynamic range of N display greyscale levels. The assignor compresses the larger number of M camera greyscale levels into the smaller number of N display greyscale levels by assigning more than one camera greyscale levels into a single display greyscale level. A direct compression may involve assigning two camera greyscale levels (or some other multiple) into each display greyscale level. A more complex compression may involve two (or more) compression ratios such as 2 and 3, or 3 and 4 which are staggered with each display greyscale level. In a no compression embodiment, the assignment ratio between the camera greyscale levels and the display greyscale levels is 1:1.

INTERVAL CORRECTION (FIG. 3)

The plurality of C calibrated attenuators may include a series of intermediate calibrated attenuators as shown in the embodiment of FIG. 2. The intermediate calibrated attenuators provide a series of intermediate attenuations between the high attenuation and the low attenuation. The intermediate attenuations may be of progressively decreasing attenuation in a series of predetermined step changes in attenuation. The series of intermediate attenuators exhibit a series of progressively decreasing intermediate calibrated greyscale levels spaced at greyscale intervals along the camera greyscale between the high calibrated greyscale level and the low calibrated greyscale level.

Greyscale interval checker 34C receives the high calibrated greyscale level and the intermediate calibrated greyscale levels and the low calibrated greyscale level from retriever 32. The interval checker compares the intervals of greyscale levels between the calibrated greyscale levels with the predetermined attenuation step changes between the high attenuation and the intermediate attenuations and the low attenuation. Interval corrector 34D corrects greyscale distortion by adjusting the intermediate greyscale intervals to coincide with the intermediate attenuation step changes. The greyscale distortion may be due to lack of contrast fidelity within the system, such as a non-linearity in the camera detectors. Greyscale distortion may also be caused by non-uniform radiation distribution from the X-ray source. The X-ray intensity around the edges of the X-ray field of view may be greater near the center than around the edges.

Figure 4A:
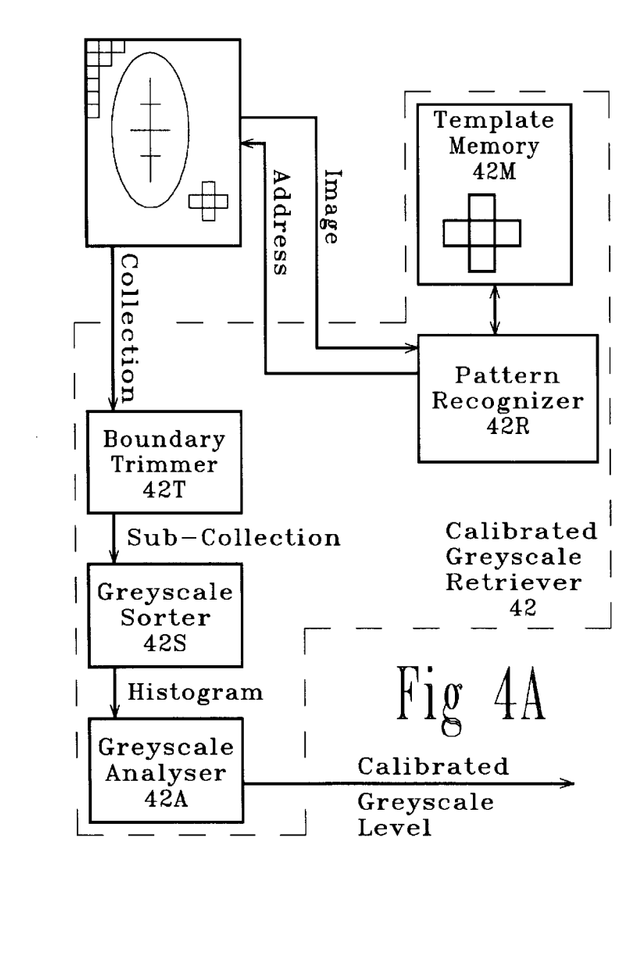
FIG. 4A is a block diagram of calibrated greyscale retriever 42 employing boundary trimming and greyscale histograms for analyzing the calibrated greyscale levels.
Figure 4B:
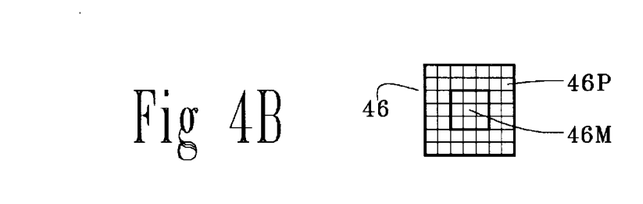
FIG. 4B shows a simple calibrated attenuator image formed by a 7×7 pixel collection trimmed to a 3×3 sub-collection having nine pixels.

BOUNDARY EFFECTS (FIGS. 4A and 4B)

The attenuator pixel collection may have a main region of inner pixels and a peripheral region of outer pixels around the main region. The outer pixels may be discarded to eliminate irregular boundary effects around the periphery of the collection. These boundary effects may be caused by reduced greyscale pixels around the attenuator, or skewed alignment between the attenuator and the camera pixel grid, or mechanical vibration of the source or the attenuator or the camera. The inner pixels are isolated from these edge effects by the peripheral region. The shape of the pixel collections and the pixel dimensions of the main region and the peripheral region may vary depending on the application of the X-ray imaging system. For example, a pixel collection may be in the form of a 32×32 pixel square, with a four pixel wide peripheral region of outer pixels, leaving a 28×28 pixel main region of inner pixels. However, for convenience of illustration, pixel collection 46 (shown in FIG. 4) is a 7×7 pixel square, with a two pixel wide peripheral region 46P and a 3×3 pixel main region 46M defining a sub-collection of nine inner pixels. Boundary trimmer 42T discards the outer pixels reducing each attenuator pixel collection to a sub-collection of inner pixels which are free from edge effects.

HISTOGRAM ANALYSIS (FIGS. 4A 4C 4D and 4E)

Greyscale sorter 42S sorts the greyscale levels forming each attenuator pixel collection by greyscale to provide a histogram (greyscale level verses level frequency) for each pixel collection. Greyscale analyzer 42A analyzes each histogram of sorted greyscale levels to identify the prevailing calibrated greyscale level for each pixel collection.

Figure 4C:
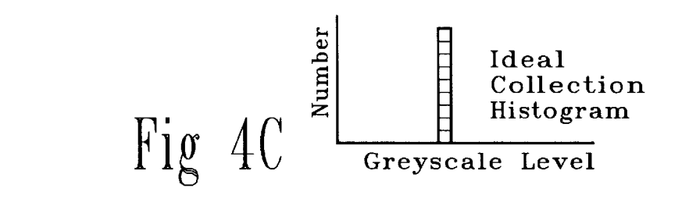
FIG. 4C is an ideal greyscale histogram of the sub-collection of FIG. 4B showing nine pixels at the same greyscale level.
Figure 4D:
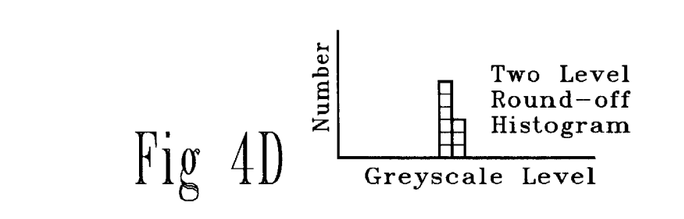
FIG. 4D is a greyscale histogram of the sub-collection of FIG. 4B showing six pixels at one greyscale level and three pixels at an adjacent greyscale level caused by A/D conversion in the camera detectors.
Figure 4E:
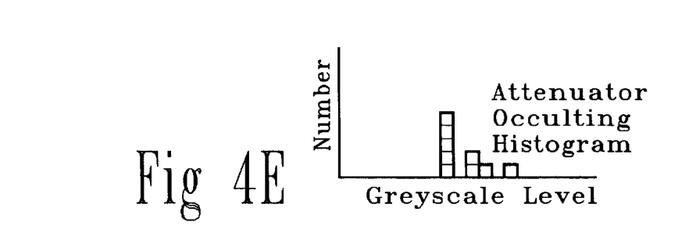
FIG. 4E is a greyscale histogram of the sub-collection of FIG. 4B showing five pixels at a prevailing level and other pixels and higher levels caused by occulting of the calibrated attenuator.

FIG. 4C is a greyscale histogram of an ideal nine pixel sub-collection from main region 46M after peripheral region 46P has been discarded. These inner pixels have the same greyscale level, which is readily analyzed as the prevailing greyscale level for the attenuator sub-collection. FIG. 4D is a greyscale histogram of a non-ideal pixel sub-collection with two adjacent prevailing levels, a major prevailing level and a minor prevailing level. Of the nine inner pixels, six pixels are at the major greyscale level and three pixels are at an adjacent minor greyscale level. The major greyscale level is analyzed as the correct prevailing greyscale level for the attenuator sub-collection. FIG. 4E is a greyscale histogram of a degraded pixel collection showing the effects of occulting interference of the calibrated attenuator image. The calibrated attenuator has been partially blocked from the camera by the subject or a foreign object. Of the nine inner pixels, five pixels at the same lower level and the remaining four pixels have been degraded to higher levels. The five pixel level is analyzed as the prevailing greyscale level for the attenuator sub-collection.

Figure 5:
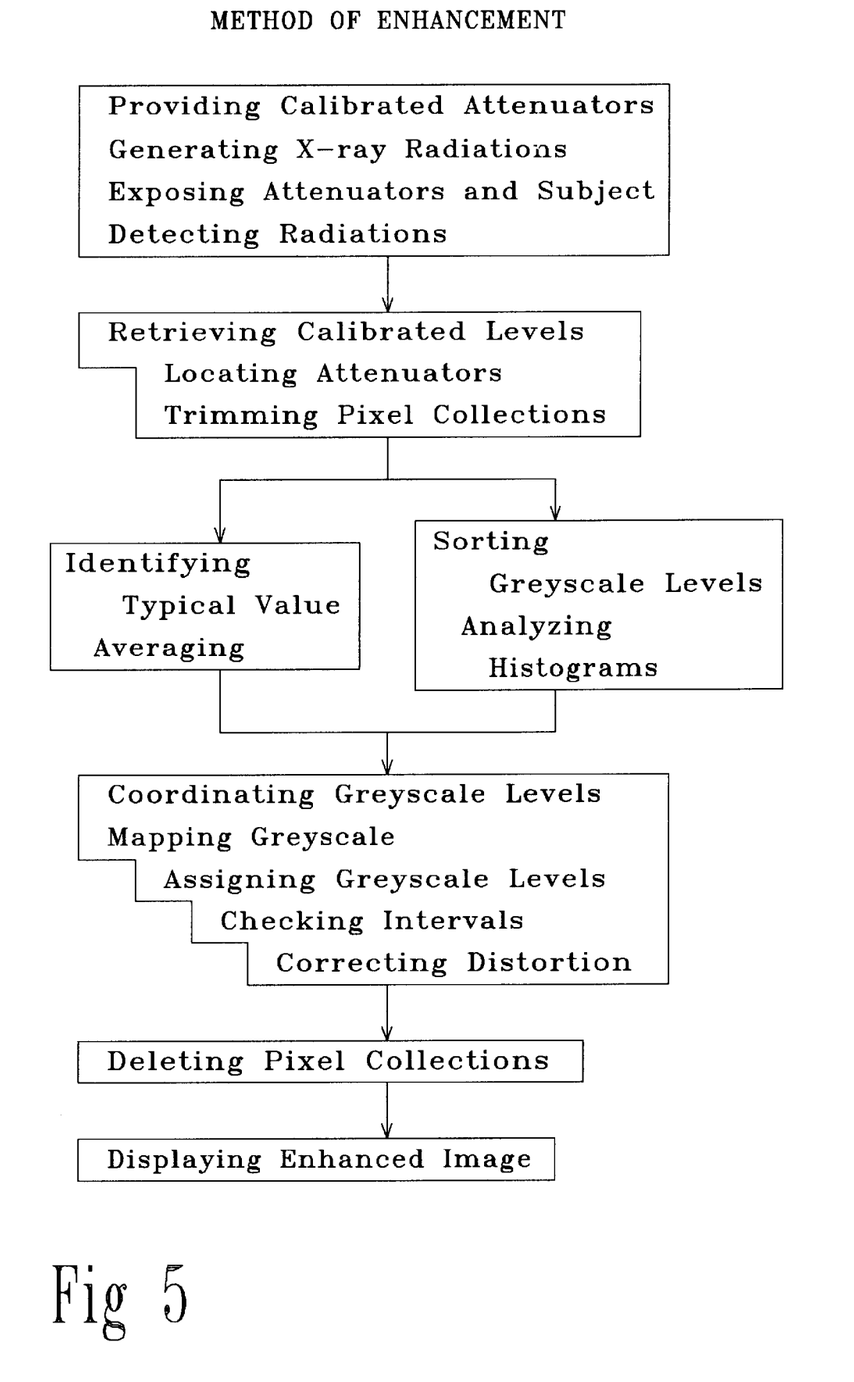
FIG. 5 is a flow chart showing the steps in a general method of enhancing a digital display image.

METHOD OF ENHANCEMENT (FIG. 5)

The steps of the general method of X-ray imaging for automatically enhancing a digital display image from a digital camera image showing internal structure of interest within a subject, are shown in the flow chart of FIG. 5. The apparatus required for carrying out the above method is disclosed in connection with the detailed description of FIGS. 1 through 4E. The steps of the method are described below.

Providing a plurality of calibrated attenuators each having an attenuation which has been calibrated against a known reference attenuation.

Generating X-ray radiations which become calibrated attenuated radiations and differential attenuated radiations.

Exposing the calibrated attenuators and the subject to the X-ray radiations to cause the calibration and differentiation. The middle position of the selected dynamic range within the full camera greyscale is affected by the camera exposure time, and also by the intensity and energy of the X-ray radiations from the X-ray source. Over exposure due to a long exposure time shifts the dynamic range into the lower greyscale levels (toward the left in the diagram of FIG. 2). Under exposure due to a short exposure time shifts the dynamic range into the higher greyscale levels (toward the right in the diagram of FIG. 2). Figure shows the traditional negative X-ray format in which bones and other dense structure appears light and soft tissue appears dark. A non-traditional positive format may be employed in which light and dark is reversed. That is, bone appears dark and tissue appears light.

Detecting the calibrated and differential radiations. The calibrated attenuated radiations provide a plurality of calibrated greyscale levels, and the differentially attenuated radiations provide the digital camera image of internal structure of the subject formed by pixels at greyscale levels within the camera greyscale.

Retrieving a calibrated greyscale level from the camera image for each attenuator pixel collection.

Coordinating the greyscale for determining mapping assignments defining the relationship between the camera greyscale and the display greyscale;

Mapping the greyscale in response to the mapping assignments for mapping the camera greyscale levels into display greyscale levels.

Displaying the enhanced digital display image of internal structure of interest within the subject employing the display greyscale.

Deleting the attenuator pixel collections from the enhanced display image before displaying the enhanced display image in order to remove the image of the calibrated attenuators from the enhanced display image. The image of the calibrated attenuator is not essential to the display internal structure of interest. Once the calibrated greyscale levels contained in the image of the calibrated attenuators have been employed to automatically enhance the display image, the entire calibrated attenuator image may be eliminated from the display image.

Additional Coordinating Steps

The coordinating step may have the following the additional steps.

Greyscale assigning the M camera greyscale levels of the selected dynamic range among the N display greyscale levels of the display dynamic range, permitting the mapper to map the camera image into the enhanced display image.

Checking greyscale intervals between a high calibrated greyscale level and intermediate calibrated greyscale levels and a low calibrated greyscale level, against predetermined attenuation step changes between the high attenuation and the intermediate attenuations and the low attenuation.

Correcting camera greyscale distortion by adjusting the intermediate greyscale intervals to coincide with the intermediate attenuation step changes.

Additional Retrieving Steps

The retrieving step may have the following the additional steps.

Locating the calibrated attenuators for providing the address of each attenuator pixel collection within the camera image corresponding to the position of each calibrated attenuator, in order to retrieve the calibrated greyscale levels from the determined addresses.

Recognizing a predetermined pattern of the attenuator pixel collections within the camera image in responsive to a memory template to determine the addresses of the pixel collections.

Identifying a typical value of the greyscale level within each attenuator pixel collection indicating the prevailing greyscale value of that pixel collection.

Sorting the greyscale levels forming each attenuator pixel collection by greyscale.

Analyzing the sorted greyscale levels to identify the prevailing calibrated greyscale level for each pixel collection.

Trimming each attenuator pixel collection for discarding the outer pixels reducing each pixel collection to a subcollection of inner pixels which are sorted by the sorter.

Further, the features of this invention may be incorporated into a suitable computer readable media which stores computer instructions for causing a computer to enhance a digital display image.

CONCLUSION

It will be apparent to those skilled in the art that the objects of this invention have been achieved as described hereinbefore.

Clearly various changes may be made in the structure and embodiments shown herein without departing from the concept of the invention. Further, features of the embodiments shown in the various figures may be employed with the embodiments shown in the other figures. For instance, sorting is a basic feature which may be employed independently of pattern recognition or boundary trimming and concurrently with interval correction. Recognition may be employed with greyscale averaging or interval correction.

Therefore, the scope of the invention is to be determined by the terminology of the following claims and the legal equivalents thereof.

What is claimed is:

1. Digital X-ray imaging system which automatically provides an enhanced digital display image formed by display greyscale from a digital camera image formed by camera greyscale showing internal structure of interest within a subject, comprising:

plurality of calibrated radiation attenuators, each calibrated against a known reference attenuation;

X-ray source for generating X-ray radiations which are attenuated within the calibrated attenuators to provide calibrated attenuations, and which are differentially attenuated within the interior of the subject to reveal internal structure therein;

digital X-ray camera for detecting the calibrated radiations as a plurality of calibrated greyscale levels, and for detecting the differentially attenuated radiations to provide the digital camera image of internal structure of the subject formed by pixels at greyscale levels within the camera greyscale, each calibrated attenuator appears in the digital camera image as a collection of adjacent camera pixels exhibiting one of the plurality of calibrated greyscale levels within the camera greyscale;

retriever for retrieving a calibrated greyscale level from the digital camera image for each of the attenuator pixel collections;

greyscale coordinator responsive to the retrieved calibrated greyscale levels for determining mapping assignments defining the relationship between the camera greyscale and the display greyscale to provide the enhanced digital display image;

greyscale mapper responsive to the mapping assignments from the coordinator for mapping the camera greyscale levels of the camera pixels forming the digital camera image into display greyscale levels forming the enhanced display image; and pixel display device responsive to the enhanced display image for displaying a pixel image of internal structure of interest within the subject.

2. The system of claim 1, wherein the plurality of calibrated attenuators includes:

a high attenuator with a high attenuation exhibiting a high calibrated greyscale level near the maximum opacity of internal structure of interest within the subject; and a low attenuator with a low attenuation exhibiting a low calibrated greyscale level near the maximum transparency of internal structure of interest within the subject.

3. The system of claim 2, wherein the camera greyscale levels exhibited by internal structure of interest extend from the high attenuation calibrated greyscale level to the low attenuation calibrated greyscale level defining a selected dynamic range of "M" camera greyscale levels which includes the calibrated greyscale levels.

4. The system of claim 3, wherein:

the enhanced display image displayed on the pixel display device has a high enhanced greyscale level mapped from the high calibrated greyscale level, and a low enhanced greyscale level mapped from the low calibrated greyscale level; and the enhanced greyscale levels of the display image extend from the high greyscale level to the low greyscale level defining a dynamic range of "N" display greyscale levels.

5. The system of claim 4, wherein the coordinator further comprises a greyscale assignor for assigning the M camera greyscale levels of the selected dynamic range among the N display greyscale levels of the display dynamic range, permitting the mapper to map the digital camera image into the enhanced display image.

6. The system of claim 5, wherein the selected dynamic range of M camera greyscale levels has more greyscale levels than the display dynamic range of N display greyscale levels, and the assignor compresses the larger number of M camera greyscale levels into the smaller number of N display greyscale levels by assigning more than one camera greyscale levels into a single display greyscale level.

7. The system of claim 5, wherein the plurality of calibrated attenuators includes a series of intermediate calibrated attenuators providing a series of intermediate attenuations between the high attenuation and the low attenuation, of progressively decreasing attenuation in a series of predetermined step changes in attenuation, the series of intermediate attenuators exhibiting a series of progressively decreasing intermediate calibrated greyscale levels spaced at greyscale intervals along the camera greyscale between the high calibrated greyscale level and the low calibrated greyscale level.

8. The system of claim 7, further comprising:
 a greyscale interval checker for receiving the high calibrated greyscale level and the intermediate calibrated greyscale levels and the low calibrated greyscale level from the retriever, for comparing the intervals of greyscale levels between the calibrated greyscale levels with the predetermined attenuation step changes between the high attenuation and the intermediate attenuations and the low attenuation; and
 an interval corrector for correcting greyscale distortion by adjusting the intermediate greyscale intervals to coincide with the intermediate attenuation step changes.

9. The system of claim 1, wherein the retriever comprises a calibrated attenuator locator for providing the address of each attenuator pixel collection within the digital camera image corresponding to the position of each calibrated attenuator, in order to retrieve the calibrated greyscale levels from the determined addresses.

10. The system of claim 9, wherein the position of each calibrated attenuator is fixed relative to the camera causing each attenuator pixel collection to have a corresponding dedicated address within the digital camera image.

11. The system of claim 9, wherein:
 the position of each calibrated attenuator is variable relative to the camera causing each attenuator pixel collection to have a corresponding variable address within the digital camera image; and
 the calibrated attenuators are arranged in a predetermined pattern relative to each other.

12. The system of claim 11, wherein the locator comprises:
 a template memory containing a template of the predetermined pattern arrangement of the calibrated attenuators; and
 pattern recognizer responsive to the template and to the digital camera image, for recognizing the predetermined pattern to determine the addresses of the attenuator pixel collections within the digital camera image.

13. The system of claim 9, wherein the retriever further comprises:
 an averager for determining the average value of the greyscale level within each attenuator pixel collection; and
 an average rounder for reducing the average to an integer value indicating a single greyscale level.

14. The system of claim 9, wherein the retriever further comprises:
 a greyscale sorter for sorting the greyscale levels forming each attenuator pixel collection by greyscale; and
 a greyscale analyzer for analyzing the sorted greyscale levels from the sorter forming each pixel collection to identify the prevailing calibrated greyscale level for each pixel collection.

15. The system of claim 14, wherein each attenuator pixel collection has a main region of inner pixels and a peripheral region of outer pixels around the main region.

16. The system of claim 15, wherein the retriever further comprises a boundary trimmer for discarding the outer pixels reducing each attenuator pixel collection to a subcollection of inner pixels which are sorted by the sorter.

17. Method of digital X-ray imaging which automatically provides an enhanced digital display image formed by display greyscale from a digital camera image formed by camera greyscale showing internal structure of interest within a subject, comprising the steps of:
 providing a plurality of calibrated attenuators each having an attenuation which has been calibrated against a known reference attenuation;
 generating X-ray radiations at least some of which are calibratedly attenuated within the interior of the calibrated attenuators, and at least some of which are differentially attenuated within the interior of the subject to reveal internal structure thereof;
 exposing the plurality of calibrated attenuators and the subject to the generated X-ray radiations to effect the calibrated attenuated radiations within the calibrated attenuators, and to produce the differentially attenuated radiations within the subject;
 detecting the calibrated attenuated radiations to provide a plurality of calibrated greyscale levels and the differentially attenuated radiations to provide the digital camera image of internal structure of the subject formed by pixels at greyscale levels within the camera greyscale, each calibrated attenuator appears in the digital camera image as a collection of adjacent camera pixels exhibiting one of the plurality of calibrated greyscale levels within the camera greyscale;
 retrieving a calibrated greyscale level from the digital camera image for each of the attenuator pixel collections;
 coordinating the greyscale in response to the retrieved calibrated greyscale levels for determining mapping assignments defining the relationship between the camera greyscale and the display greyscale;
 mapping the greyscale in response to the mapping assignments from the coordinator for mapping the camera greyscale levels of the camera pixels forming the digital camera image into display greyscale levels of display pixels forming the enhanced display image; and
 displaying the enhanced display image of internal structure of interest within the subject employing the display greyscale.

18. The method of claim 17, wherein the plurality of calibrated attenuators includes:
 a high attenuator with a high attenuation exhibiting a high calibrated greyscale level near the maximum opacity of internal structure of interest within the subject; and
 a low attenuator with a low attenuation exhibiting a low calibrated greyscale level near the maximum transparency of internal structure of interest within the subject.

19. The method of claim 18, wherein:
the camera greyscale levels exhibited by internal structure of interest extend from the high attenuation calibrated greyscale level to the low attenuation calibrated greyscale level defining a selected dynamic range of "M" camera greyscale levels; and
the enhanced display image displayed on the pixel display device has a high enhanced greyscale level mapped from the high calibrated greyscale level, and a low enhanced greyscale level mapped from the low calibrated greyscale level, the enhanced greyscale levels of the display image extend from the high greyscale level to the low greyscale level defining a dynamic range of "N" display greyscale levels.

20. The method of claim 19, wherein the coordinating step further comprises the additional step of greyscale assigning the M camera greyscale levels of the selected dynamic range among the N display greyscale levels of the display dynamic range, permitting the mapper to map the digital camera image into the enhanced display image.

21. The method of claim 20, wherein:
the selected dynamic range of M camera greyscale levels has more greyscale levels than the display dynamic range of N display greyscale levels; and
the assignor compresses the larger number of M camera greyscale levels into the smaller number of N display greyscale levels by assigning more than one camera greyscale levels into a single display greyscale level.

22. The method of claim 20, wherein the plurality of calibrated attenuators includes a series of intermediate calibrated attenuators with a series of intermediate attenuations between the high attenuation and the low attenuation, of progressively decreasing attenuation in a series of predetermined step changes in attenuation, the series of intermediate attenuators exhibiting a series of progressively decreasing intermediate calibrated greyscale levels spaced at greyscale intervals along the camera greyscale between the high calibrated greyscale level and the low calibrated greyscale level.

23. The method of claim 22, wherein the coordinating step further comprises the additional steps of:
checking the intervals between the high calibrated greyscale level and the intermediate calibrated greyscale levels and the low calibrated greyscale level, against the predetermined attenuation step changes between the high attenuation and the intermediate attenuations and the low attenuation; and
correcting camera greyscale distortion by adjusting the intermediate greyscale intervals to coincide with the intermediate attenuation step changes.

24. The method of claim 17, wherein the retrieving step further comprises the additional step of locating the plurality of calibrated attenuators for providing the address of each attenuator pixel collection within the digital camera image corresponding to the position of each calibrated attenuator, in order to retrieve the calibrated greyscale levels from the determined addresses.

25. The method of claim 24, wherein the locating step further comprises the additional step of recognizing a predetermined pattern of the attenuator pixel collections within the digital camera image in responsive to a memory template to determine the addresses of the pixel collections.

26. The method of claim 17, wherein the retrieving step further comprises the additional step of identifying a typical value of the greyscale level within each attenuator pixel collection indicating the prevailing greyscale value of that pixel collection.

27. The method of claim 17, wherein the retrieving step further comprises the additional steps of:
sorting the greyscale levels forming each attenuator pixel collection by greyscale; and
analyzing the sorted greyscale levels to identify the prevailing calibrated greyscale level for each pixel collection.

28. The method of claim 27, wherein each attenuator pixel collection has a main region of inner pixels and a peripheral region of outer pixels around the main region.

29. The method of claim 28, wherein the retrieving step further comprises the additional step of trimming each attenuator pixel collection for discarding the outer pixels reducing each pixel collection to a sub-collection of inner pixels which are sorted by the sorter.

30. The method of claim 17, further comprising the additional step of deleting the attenuator pixel collections from the enhanced display image before displaying the enhanced display image in order to remove the image of the calibrated attenuators from the enhanced display image.

31. Digital X-ray enhancement system which automatically provides an enhanced digital display image formed by display greyscale from a digital camera image formed by camera greyscale showing internal structure of interest within a subject for display on a display device, in response to X-ray radiations which are differentially attenuated within the interior of the subject to reveal internal structure therein, and which X-ray radiations are detected by a digital X-ray camera to provide the digital camera image of internal structure of the subject formed by pixels at greyscale levels within the camera greyscale, comprising:
calibrated radiation attenuator means calibrated against a known reference attenuation, which attenuate the X-ray radiations to provide calibrated attenuations for detection by the X-ray camera as a plurality of calibrated greyscale levels, each calibrated attenuator means appears in the digital camera image as a collection of adjacent camera pixels exhibiting one of the plurality of calibrated greyscale levels within the camera greyscale;
retriever means for retrieving a calibrated greyscale level from the digital camera image for each of the attenuator pixel collections;
greyscale coordinator means responsive to the retrieved calibrated greyscale levels for determining mapping assignments defining the relationship between the camera greyscale and the display greyscale to provide the enhanced digital display image; and
greyscale mapper means responsive to the mapping assignments from the coordinator for mapping the camera greyscale levels of the camera pixels forming the digital camera image into display greyscale levels forming the enhanced display image.

32. A computer readable medium containing a computer program that automatically provides an enhanced digital display image formed by display greyscale from a digital camera image of digital X-ray image formed by camera greyscale showing internal structure of interest within a subject, by directing a computer to execute the steps of:
providing a plurality of calibrated attenuators each having an attenuation which has been calibrated against a known reference attenuation;

generating X-ray radiations at least some of which are calibratedly attenuated within the interior of the calibrated attenuators, and at least some of which are differentially attenuated within the interior of the subject to reveal internal structure thereof;

exposing the plurality of calibrated attenuators and the subject to the generated X-ray radiations to effect the calibrated attenuated radiations within the calibrated attenuators, and to produce the differentially attenuated radiations within the subject;

detecting the calibrated attenuated radiations to provide a plurality of calibrated greyscale levels and the differentially attenuated radiations to provide the digital camera image of internal structure of the subject formed by pixels at greyscale levels within the camera greyscale, each calibrated attenuator appears in the digital camera image as a collection of adjacent camera pixels exhibiting one of the plurality of calibrated greyscale levels within the camera greyscale;

retrieving a calibrated greyscale level from the digital camera image for each of the attenuator pixel collections;

greyscale coordinating in response to the retrieved calibrated greyscale levels for determining mapping assignments defining the relationship between the camera greyscale and the display greyscale;

greyscale mapping in response to the mapping assignments from the coordinator for mapping the camera greyscale levels of the camera pixels forming the digital camera image into display greyscale levels of display pixels forming the enhanced display image; and displaying the enhanced display image of internal structure of interest within the subject employing the display greyscale.

\* \* \* \* \*

UNITED STATES PATENT AND TRADEMARK OFFICE
CERTIFICATE OF CORRECTION

PATENT NO. : 6,292,535 B1
DATED : September 18, 2001
INVENTOR(S) : Neil A. Williams et al.

It is certified that error appears in the above-identified patent and that said Letters Patent is hereby corrected as shown below:

Column 2,
Line 26, "other" should read -- others --.

Column 5,
Line 22, "frail elderly" should read -- frail, elderly, --; and
Line 64, "retrieved" should read -- retrieved from --.

Column 6,
Line 15, "other." should read -- another. --;
Line 20, "to shapes" should read -- shapes --;
Line 39, "valuation" should read -- valuations --; and
Line 49, "the in" should read -- the --.

Column 8,
Line 43, "structure appears" should read -- structures appear --; and
Line 45, "is" should read -- are --.

Column 13,
Line 18, "camer a" should read -- camera --.

Signed and Sealed this

Eighteenth Day of February, 2003

JAMES E. ROGAN
*Director of the United States Patent and Trademark Office*